United States Patent [19]
Ito et al.

[11] Patent Number: 5,258,787
[45] Date of Patent: Nov. 2, 1993

[54] OPHTHALMOLOGIC APPARATUS

[75] Inventors: Kosuke Ito, Toyohashi; Yoshikatsu Suzumura, Gamagouri, both of Japan

[73] Assignee: Kowa Company Ltd., Japan

[21] Appl. No.: 919,971

[22] Filed: Jul. 27, 1992

Related U.S. Application Data

[63] Continuation of Ser. No. 595,232, Oct. 10, 1990, abandoned.

[30] Foreign Application Priority Data

Oct. 16, 1989 [JP] Japan .................................. 1-266248

[51] Int. Cl.[5] ............................................. A61B 3/10
[52] U.S. Cl. .................................. 351/214; 351/205; 351/221; 359/432
[58] Field of Search ............... 351/205, 206, 207, 208, 351/214, 236, 221; 359/432

[56] References Cited

U.S. PATENT DOCUMENTS

| | | | |
|---|---|---|---|
| 3,259,039 | 7/1966 | Okajima | 351/206 |
| 3,535,027 | 7/1968 | Littmann et al. | 351/221 X |
| 4,779,969 | 10/1988 | Sato et al. | 359/432 X |

FOREIGN PATENT DOCUMENTS 8900298  1/1989  PCT Int'l Appl. .................. 351/221

Primary Examiner—Bruce Y. Arnold
Assistant Examiner—Hung Xuan Dang
Attorney, Agent, or Firm—Bruce L. Adams; Van C. Wilks

[57] ABSTRACT

In an ophthalmologic apparatus comprises an illumination optical system for directing illumination light onto a prescribed point of an eye under examination, and an observation optical system for observing an image of the prescribed point of the eye under examination formed through an object lens. The object lens is movably supported along its optical axis between a first position at which the image point falls at its object point and a second position at which the prescribed point of the eye under examination falls at its image point. As a result, there is a change in the conjugate relationship so that a sharply focused image can be observed when the object lens is at either position thereby making it possible to observe sharply focused images of different magnifications simply by moving the object lens.

5 Claims, 2 Drawing Sheets

OPHTHALMOLOGIC APPARATUS

This is a continuation application of parent application Ser. No. 595,232 filed Oct. 10, 1990, now abandoned.

BACKGROUND OF THE INVENTION

1. Filed of the Invention

This invention relates to an ophthalmologic apparatus, and more particularly to an ophthalmologic apparatus comprising an illumination optical system for directing illumination light onto a prescribed point of an eye under examination and an observation optical system for observing an image of the prescribed point of the eye under examination formed through an object lens.

2. Description of the Prior Art

In conventional apparatuses used in ophthalmological treatment such as the slit lamp microscope, white light from a light source, such as a halogen lamp is passed through a slit formed between the opposing edges of two shield plates. The slit beam obtained in this way is directed onto a prescribed point on the cornea, crystalline lens or the like of the eye under examination. The scattered light from the illuminated point passes through an object lens of an observation optical system and the resulting image of the point can be observed for examining the condition of the cornea, crystalline lens etc.

One method used for varying the magnification factor in order to enlarge or reduce the observed image has been to insert or remove a lens into or from the observation optical system. However, this method requires a mechanism for insertion and removal of lenses and thus increases the complexity of the overall structure of the apparatus. Other methods that have been used for this purpose include one in which magnification of the observed image is varied by loading lenses into a turret and then rotating the turret to bring a lens of the required power into the light path. In another method the magnification is varied by moving a zoom lens built into the observation optical system along the optical axis. With either of these arrangements, however, the number of lenses is increased and it becomes necessary to control the lens intervals and decentering, which increases the complexity of the apparatus and increases its weight.

SUMMARY OF THE INVENTION

An object of the present invention is to alleviate the drawbacks of the prior art. Another object is to provide an ophthalmologic apparatus which is able to vary the magnification of the observed image of the eye under examination by means of a simple, mechanism. The present invention provides an ophthalmologic apparatus comprising illuminating means or an illumination optical system for directing illumination light onto a prescribed point of an eye under examination The present invention also provides observating means or an observation optical system for observing at an observation point an image of the prescribed point of the eye under examination formed through a movable object lens moving means is provided for moving the object lens is made movable along its optical axis between a position at which said image point falls at its object point and a position at which the prescribed point of the eye under examination falls at its image point.

With this arrangement, the observation point of the eye under examination falls at the object point of the object lens of the observation optical system and the image point falls at the conjugate point thereof. If the object lens is moved along the optical axis between one position at which the aforesaid image point falls at the image point of the object lens and another position at which the observation point of the eye under examination falls at the image point, then since there is no change in the conjugate relationship, a sharp image can be observed in either case. In this case, the distances from the object point and the image point to the object lens are different before and after the object lens is moved so that the magnification of the observed image changes. It is thus possible to observe sharp images of different magnification simply by moving the object lens.

BRIEF DESCRIPTION OF THE DRAWINGS

The objects and features of the present invention will become more apparent from a consideration of the following description taken in conjunction with the accompanying drawings in which.

DETAILED DESCRIPTION OF THE PREFERRED EMBODIMENTS

The invention will now be described with reference to the attached drawings.

Figure 1:
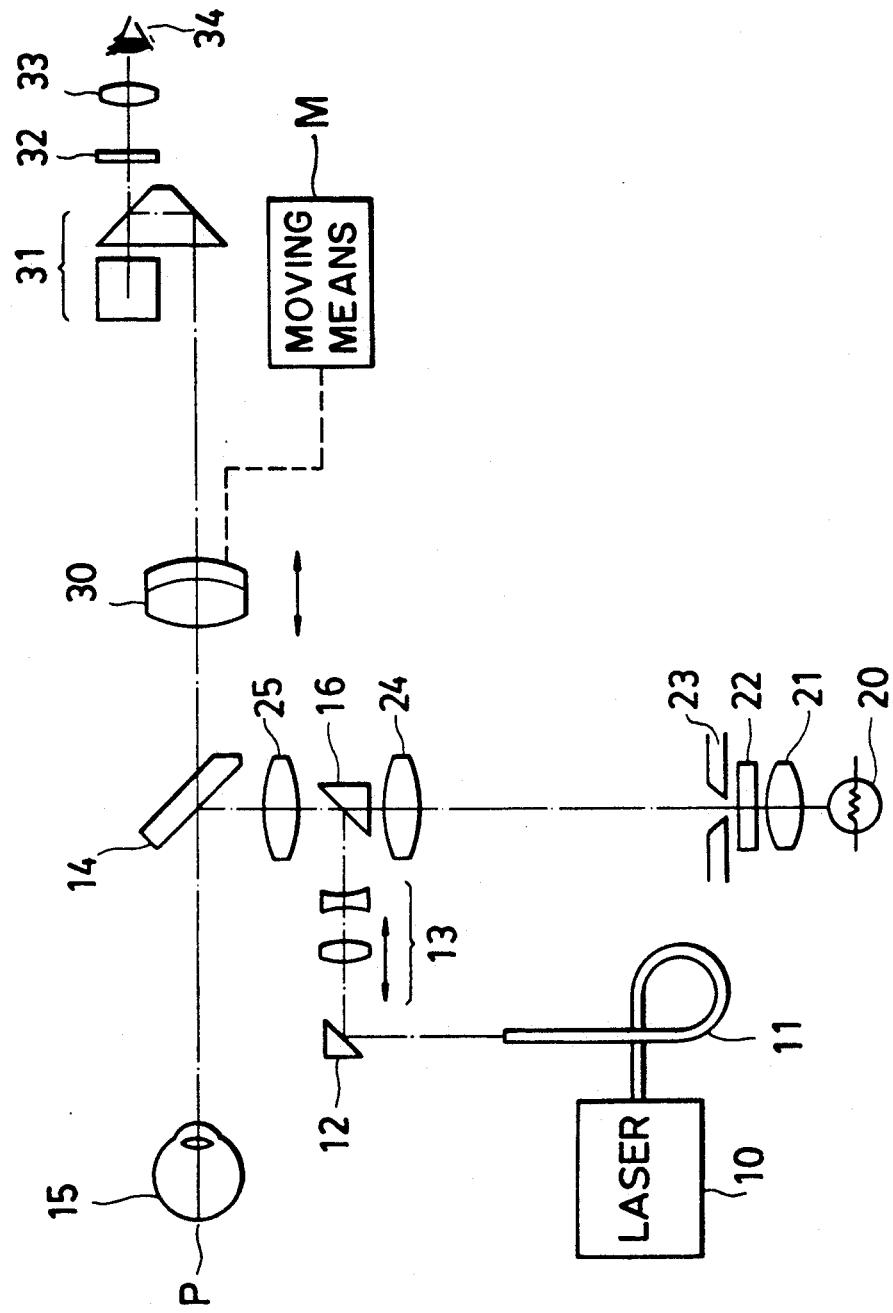
FIG. 1 is a diagram showing the general configuration of the apparatus according to the invention.

FIG. 1 shows an embodiment of the invention in which the ophthalmologic apparatus is applied to a laser beam coagulation apparatus. A laser beam emitted by a laser beam source 10 is projected through an optical fiber onto a mirror 12 from which it is reflected onto a mirror 16 through a laser beam projection lens system 13. From the mirror 12, the laser beam precedes through a lens 25 to a scanning mirror 14 which deflects it toward an eye under examination 15 for illuminating a prescribed point P of the eye 15.

Figure 2:
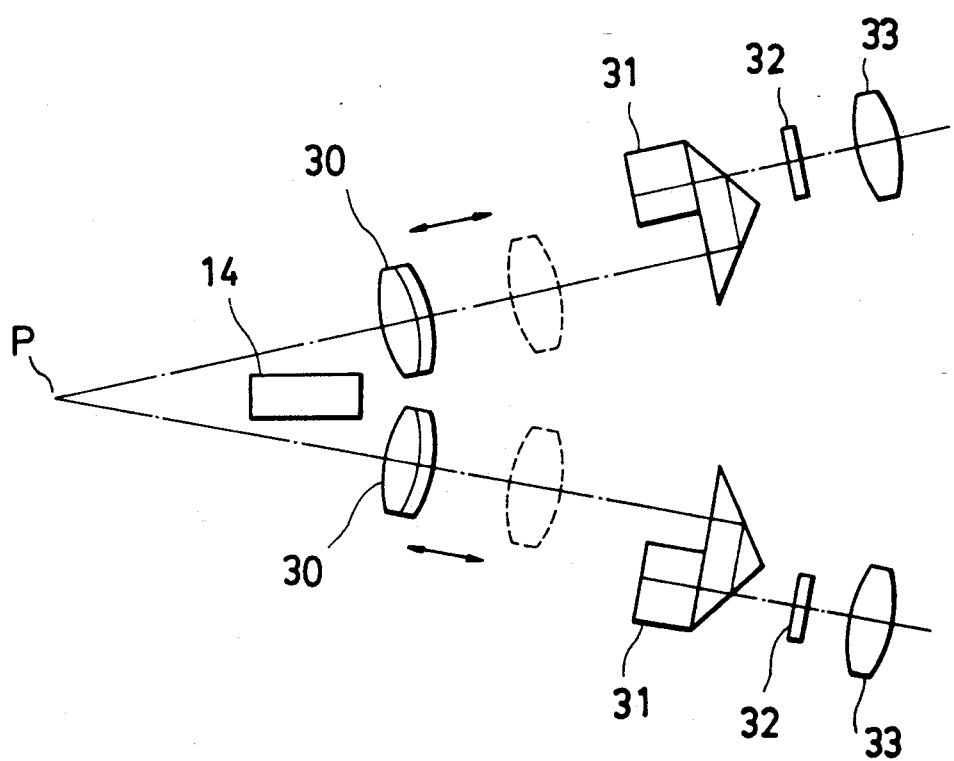
FIG. 2 is a diagram showing the arrangement of the observation optical system of the apparatus of FIG. 1.

The apparatus is further equipped with a slit illumination optical system having a lamp 20, the light from which passes through a condenser lens 21 and a heat-absorbing filter 22 and illuminates a slit 23. After passing through the slit 23, the slit beam precedes through the lenses 24, 25 to the scanning mirror 14 and then forms a slit image at the prescribed point P of the eye under examination 15. The fundus image illuminated by the slit beam precedes through the scanning mirror 14 and an object lens 30 to an observation optical system comprising an erect prism 31, a reticle 32 and an eyepiece 33, for use in observation by an observer 34. As shown in FIG. 2, two sets of the object lens 30, the erect prism 31, reticle 32 and erect prism 31 are provided, one for each eye of the observer 34. For the sake of simplicity of explanation, however, the following description will be made with respect to only one side of the observation optical systems.

As shown by the solid and broken lines in FIG. 2, each object lens 30 of the observation optical system is constituted so as to be alternately movable by moving means M between a first position and a second position.

With this arrangement of the apparatus, when the object lens is in the position indicated by solid lines, the point P illuminated by the slit image formed on the fundus of the eye under examination 15 is observed through the observation optical system by the observer. The arrangement is such that at this time (when the object lenses 30 are in the solid line positions), an image of the point P is formed at the reticle 32 and the so-formed image of P can be observed through the eyepiece 33. The magnification of the object lens 30 at this time is set to be 0.6, for example.

The position indicated by broken lines is selected such that when the object lens 30 is moved to this position, the relationship between the object point and the image point is reversed from that in the solid line position. As a result, the conjugate points are also reversed. As the conjugate relationship is maintained in this position, a sharp image of point P is again formed at the reticle 32. The magnification at this time becomes 1/0.6. In other words, this means that a sharply focused image can be observed by moving the object lens 30 from a position at which the magnification is 0.6 to a position at which the magnification is 1/0.6.

In contrast with the conventional apparatuses, in which the magnification is varied by using a built-in zoom lens or turret lens in place of the object lens, in accordance with the present invention, observation of a sharply focused image can be conducted at two different magnifications simply by moving the object lens.

While the invention has been described with respect to an embodiment applied to a laser beam coagulation apparatus, this is not limitative and the invention can be applied to the observation optical system of any type of ophthalmologic apparatus.

As is clear from the foregoing explanation, in the present invention the object lens of the observation optical system can be moved along its optical axis such that its image point will fall at the object point or that the prescribed point of the eye under examination will fall at its image point. As a result, there is no change in the conjugate relationship so that a sharply focused image can be observed in either case, making it possible to observe sharply focused images of differing magnification simply by moving the object lens.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmologic apparatus, comprising: an illumination optical system for directing illumination light onto a prescribed point of an eye under examination; an observation optical system having an observation point for observing an image of the prescribed point of the eye under examination formed through a movably mounted object lens; and moving means for moving the object lens along its optical axis alternately between two predetermined positions to obtains a focused image at alternate ones of only two different magnifications, the two predetermined positions comprising a first position at which a first focused image having a first magnification of the prescribed point is formed at the observation point and a second position, which is a conjugate of the first position, at which a second focused image having a second magnification of the prescribed point is formed at the observation point.

2. An ophthalmologic apparatus, comprising: illuminating means for illuminating a prescribed point of an eye under examination; observing means having at least one observation point for observing an image of the prescribed point and including at least one movably mounted objective lens for forming the image at a corresponding observation point; and moving means for moving the objective lens alternately between two predetermined positions to obtain a focused image at alternate ones of only two different magnifications, the two predetermined positions comprising a first position at which the image is focused at a first magnification at the corresponding observation point, and a second position at which the image is focused at a second magnification at the corresponding observation point, wherein the prescribed point and the image are conjugate to each other at the first and second positions of the objective lens.

3. An ophthalmologic apparatus according to claim 2; wherein the observing means includes two objective lenses for forming images at two corresponding observation points.

4. An ophthalmologic apparatus according to claim 2; wherein the illuminating means includes a laser.

5. An ophthalmologic apparatus according to claim 2; wherein the illuminating means includes a slit illumination optical system.

* * * * *